United States Patent [19]

Falk et al.

[11] Patent Number: 4,774,947
[45] Date of Patent: Oct. 4, 1988

[54] LITHOTRIPSY PROBE

[75] Inventors: Ernst Falk, Sternenfels-Diefenbach; Siegfried Bauer, Heidelsheim; Helmut Wurster, Oberderdingen, all of Fed. Rep. of Germany

[73] Assignee: Richard Wolf, GmbH, Fed. Rep. of Germany

[21] Appl. No.: 74,069

[22] Filed: Jul. 16, 1987

[30] Foreign Application Priority Data

Jul. 16, 1986 [DE] Fed. Rep. of Germany ... 8619055[U]

[51] Int. Cl.⁴ .............................................. A61B 17/00
[52] U.S. Cl. .................................. 128/328; 128/24.1; 128/7
[58] Field of Search ........................... 128/7, 328, 24.1

[56] References Cited

U.S. PATENT DOCUMENTS

| | | | |
|---|---|---|---|
| 3,735,764 | 5/1973 | Balev | 128/328 |
| 4,595,019 | 6/1986 | Shene | 128/328 |
| 4,605,003 | 8/1986 | Oinuma | 128/328 |
| 4,606,331 | 8/1986 | Shene | 128/24.1 |
| 4,722,340 | 2/1988 | Takayama | 128/328 |

Primary Examiner—Ronald B. Cox
Attorney, Agent, or Firm—Hill, Van Santen, Steadman & Simpson

[57] ABSTRACT

A lithotripsy probe for stone disintegration, comprising a pair of conductors insulated from one another and extending through the probe. The conductors are surrounded by a thin metal sleeve over a distal length of the probe, and the metal sleeve is provided at one point, which is situated at a distance from the distal extremity of the probe, with at least one gap or perforation in which engages an overlying shrink-on tube to immobilize the sleeve on the two insulated conductors.

4 Claims, 1 Drawing Sheet

LITHOTRIPSY PROBE

BACKGROUND OF THE INVENTION

1. Field of the Invention

This invention relates to a lithotripsy probe for stone disintegration comprising two mutually insulated conductors surrounded by a thin metal sleeve over a distal length thereof.

2. Description of the Prior Art

In the case of lithotripsy probes of the aforesaid kind which have been utilised hitherto, the metal sleeve could split throughout its length with excessive or incorrect use, e.g. in the case of more than 200 spark discharges. This split is caused by the fact that the two conductors of the probe are moved apart by the spark discharges and thereby lead to eventual tearing of the thin metal sleeve. Since there is no firm joining of the sleeve with the insulation of the conductors, the metal sleeve can under particular conditions separate from the distal extremity of the probe during the withdrawal of the probe out of the bodily cavity and remain in the patient's bodily cavity, which represents a risk to the patient.

SUMMARY OF THE INVENTION

It is accordingly an object of the invention to secure the metal sleeve situated at the distal end of the probe on the two conductors, which are insulated from each other, in such manner that it is fixedly secured notwithstanding the utilisation period and the frequency with which the probe is used.

According to the invention, this object is achieved in that the case of the lithotripsy probe referred to in the foregoing, the metal sleeve is provided with an opening at least at one point, situated at a distance from the distal extremity of the probe, and a shrink-on tube surrounds the sleeve and through the opening engages the two insulated conductors to secure the sleeve on the two insulated conductors. The engagement of the shrink-on tube may be promoted by the application of heat so that the sleeve is held at all times, and in particular during withdrawal of the probe from the bodily cavity.

In this connection, it is advantageous according to a preferred embodiment of the invention to provide several perforations or to endow or provide the metal sleeve with a coil-shaped excision or the like, the pitch of which is of a size such that the shrink-on tube which is to be fitted over it bears at least partially against the conductor insulation via the excision.

According to another embodiment of the invention, it is also possible for the metal sleeve to comprise a coil spring closely wound around the conductors at the distal extremity of the probe which in continuation thereof comprises turns with an increased pitch such that the shrink-on tube can engage in gaps between the turns to immobilise the sleeve on the two conductors.

In this case too, an indetachable fitting of the metal sleeve on the conductor wires of the probe is established thanks to which it is no longer possible for a split metal sleeve to be stripped off upon withdrawing the probe from the bodily cavity.

Further features and advantages of the invention will become apparent from the following detailed description taken in conjunction with the accompanying drawings which illustrate a preferred embodiment of the invention.

DETAILED DESCRIPTION OF THE PREFERRED EMBODIMENT

The lithotripsy probe 1 for connection to a surge wave generator is traversed in a manner known per se by two conductors 3 and 4 insulated by sleeving 2. To this end, the distal extremity is surrounded by a small thin metal tube or sleeve member to assure a constant electrode or conductor spacing during utilisation of the probe.

Figure 1:
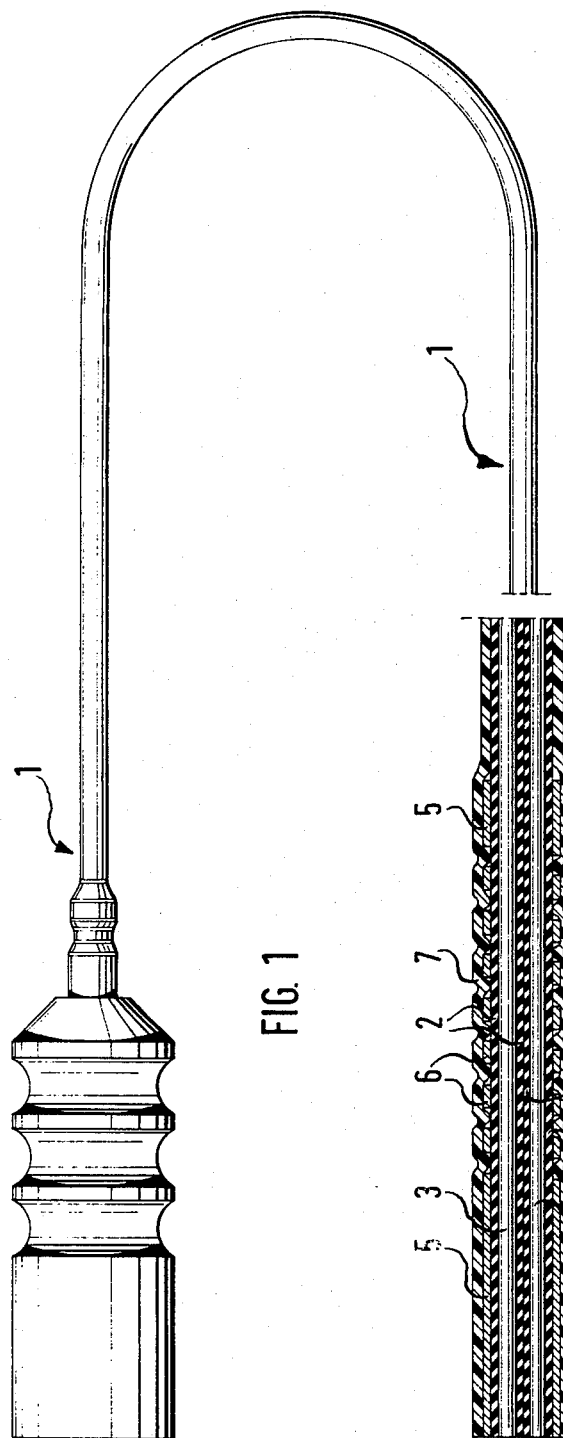
FIG. 1 is a side view of a lithotripsy probe with an axial cross-section of the distal extremity of the probe shown enlarged.
Figure 2:
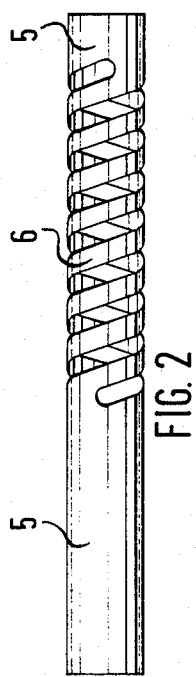
FIG. 2 is a side view of the metal sleeve utilised in FIG. 1, with helical perforations.

In accordance with the invention, the distal end of the probe has installed on it a thin metal sleeve 5 which is provided at a short distance from the distal extremity with at least one aperture or perforation and in the case of FIGS. 1 and 2, with perforations in the form of a pair of helical excisions to form a perforated section 6. This metal sleeve 5 has fitted over it a shrink-on tube 7 which under the application of heat is deformed elastically to engage in the excisions and bears directly against the insulating sleeving 2 of the two conductors 3 and 4. Thanks to this arrangement, the metal sleeve remains firmly joined to the two conductors 3 and 4 even in the case of possible splitting.

Figure 3:
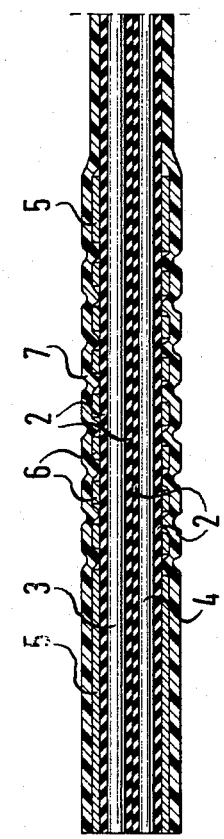
FIG. 3 is a side view of a metal sleeve of modified form, which could also be used in the embodiment of FIG. 1.
Figure 3:
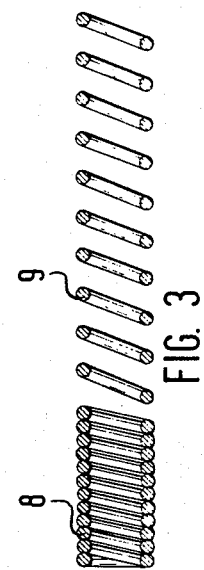

It is also possible to use a metal sleeve as shown in FIG. 3, in the form of a spring comprising turns 8 closely wound around the probe at its distal extremity, which are then proximally followed by turns 9 with an increased pitch to form gaps between successive turns. The shrink-on tube 7 which is to be fitted over the spring may penetrate between the turns 9 and bear against the insulations 2 of the two conductors 3 and 4, so that the metal sleeve is always held fast.

What is claimed is:

1. A lithotripsy probe for stone disintegration, said probe comprising two conductors insulated from one another and extending axially through the probe, a thin metal sleeve member surrounding a distal length of the probe, said sleeve member being provided with at least one aperture spaced from the distal extremity of the member, and a shrink-on tube surrounding the sleeve member, said shrink-on tube engaging the two conductors through said aperture to secure the sleeve member onto the two insulated conductors.

2. A lithotripsy probe according to claim 1, wherein said aperture comprises a helical excision.

3. A lithotripsy probe according to claim 1, wherein said sleeve has two helical excisions to form two apertures.

4. A lithotripsy probe according to claim 1, wherein said sleeve member is formed by a spring comprising a first set of turns wound closely around the distal extremity and in continuation thereof, and a second set of turns having an increased pitch relative to said first set to definine said aperture between successive turns of said second set.

* * * * *